(12) United States Patent
Bremner et al.

(10) Patent No.: US 7,849,852 B2
(45) Date of Patent: Dec. 14, 2010

(54) BREATHING ASSISTANCE APPARATUS

(75) Inventors: Michael Brian Edward Bremner, Warkworth (NZ); Lewis George Gradon, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 809 days.

(21) Appl. No.: 10/544,593

(22) PCT Filed: Feb. 3, 2004

(86) PCT No.: PCT/NZ2004/000021

§ 371 (c)(1),
(2), (4) Date: Dec. 20, 2005

(87) PCT Pub. No.: WO2004/069318

PCT Pub. Date: Aug. 19, 2004

(65) Prior Publication Data

US 2006/0213515 A1    Sep. 28, 2006

(30) Foreign Application Priority Data

Feb. 4, 2003    (NZ) ..................................... 524013

(51) Int. Cl.
*A61M 16/00*    (2006.01)
*A61M 15/00*    (2006.01)

(52) U.S. Cl. ............................. 128/204.17; 128/200.11; 128/201.13; 128/200.24; 128/203.12; 128/203.16; 128/203.17; 128/203.26; 128/203.27; 128/204.18; 128/204.21

(58) Field of Classification Search ............ 128/200.11, 128/200.13, 200.14, 200.22, 200.24, 201.13, 128/203.12, 203.16, 203.17, 203.26, 203.27, 128/204.17, 204.18, 204.21, 204.14; 239/338, 239/102.1, 102.2; 261/DIG. 26, 129, 154; 122/4 A, 5.5 A, 7 B, 13.01, 13.3–19.2, 33, 122/487, DIG. 7
See application file for complete search history.

(56) References Cited

U.S. PATENT DOCUMENTS

| 3,801,077 | A |   | 4/1974 | Pearson |
| 3,864,440 | A | * | 2/1975 | Giocoechea ............. 261/122.1 |
| 4,010,748 | A | * | 3/1977 | Dobritz ................. 128/203.27 |
| 4,110,419 | A | * | 8/1978 | Miller ........................ 261/142 |

(Continued)

*Primary Examiner*—Justine R Yu
*Assistant Examiner*—Annette F Dixon
(74) *Attorney, Agent, or Firm*—Knobbe, Martens, Olson & Bear, LLP

(57) ABSTRACT

A medical breathing assistance apparatus (20) for supplying pressurised gases to a patient is disclosed. The breathing assistance apparatus (20) comprises a heating chamber (29) and a pressure chamber (27) both adapted to contain water, and at least one pressure adjusting means (24,25,26). The pressure chamber (27) is connected to the heating chamber (29) and the pressure adjusting means (24,25,26) is located between the heating chamber (29) and a gases supplying means (23) supplying gas to both the pressure chamber (27) and heating chamber (29). The pressure adjusting means (24, 25,26) is adapted to convert pressurised gases from the gases supply means (23) to two different pressures, one to each of the heating chamber (29) and the pressure chamber (27), so that water flows from said pressure chamber (27) to the heating chamber (29).

6 Claims, 4 Drawing Sheets

U.S. PATENT DOCUMENTS

| | | | |
|---|---|---|---|
| 4,172,105 A * | 10/1979 | Miller et al. | 261/66 |
| 4,178,334 A * | 12/1979 | Miller | 261/142 |
| 4,195,044 A * | 3/1980 | Miller | 261/142 |
| 4,366,105 A * | 12/1982 | Nowacki | 261/35 |
| 4,450,118 A * | 5/1984 | Tuin | 261/147 |
| 4,500,480 A * | 2/1985 | Cambio, Jr. | 261/104 |
| 4,632,067 A * | 12/1986 | Carlson | 123/25 A |
| 4,765,327 A * | 8/1988 | Shim | 128/204.13 |
| 4,913,140 A | 4/1990 | Orec et al. | |
| 4,926,856 A | 5/1990 | Cambio, Jr. et al. | |
| 6,050,260 A * | 4/2000 | Daniell et al. | 128/204.22 |
| 6,655,383 B1 * | 12/2003 | Lundberg | 128/205.23 |
| 7,158,718 B2 * | 1/2007 | Russegger | 392/488 |
| 7,228,859 B2 * | 6/2007 | Loescher | 128/203.12 |
| 2004/0050386 A1 | 3/2004 | Levine | |

\* cited by examiner

BREATHING ASSISTANCE APPARATUS

BACKGROUND OF THE INVENTION

1. Field of the Invention

The present invention relates to components for medical breathing circuits and in particular to a humidifying apparatus to aid in the delivery of pressurised oxygen and/or air to a patient.

2. Summary of the Prior Art

A number of methods are known in the art for assisting a patient's breathing. Continuous Positive Airway pressure or CPAP involves the administration of air under pressure to a patient. It is used in the treatment of snoring and Obstructive Sleep Apnoea (OSA), a condition characterised by repetitive collapse of the upper airway during inspiration. Positive pressure splints the upper airway open, preventing its collapse. Treatment of OSA with CPAP has proven to be both effective and safe. Typically included within a CPAP device is a humidifier to humidify the air supplied to the patient, a blower to generate a positive air pressure, and a water reservoir to provide a constant supply of water to the humidifier.

For devices that use high humidity, e.g. 44 mg delivery, at relatively high flow rates, e.g. 40 litres per minute, it is preferable to use auto feed chambers that are filled from a reservoir. Common prior art devices of this type are shown in FIG. 1; these are normally used in a hospital environment but can be also used in a home environment. In particular these devices use a water reservoir 1 located above a humidification chamber 2. As the water supplied to the humidification chamber 2 is gravity fed, the water reservoir must be mounted above the humidification chamber 2 in order to create a suitable pressure differential for flow to occur. In some instances locating a reservoir above the humidification chamber 2 at a point that provides adequate pressure differential for flow to occur may not be practical (for example, if the required mounting is higher than the ceiling due to the high pressure created by the system) or is awkward as typically this is where other medical devices are located, for example drug supplies for intravenous drips.

Non-medical use humidifiers are known to have various water feeds, such as that in U.S. Pat. No. 3,801,077 and U.S. Pat. No. 4,913,140 that have a water tank or chamber that includes water feeds such that the level of the water within the tank or chamber is controlled by a float.

SUMMARY OF THE INVENTION

It is an object of the present invention to provide a breathing assistance apparatus which goes someway to overcoming the above mentioned disadvantages or which will at least provide the public with a useful choice.

Accordingly in a first aspect the present invention may broadly be said to consist in a medical breathing assistance apparatus for supplying pressurised gases to a patient comprising:

a heating chamber and a pressure chamber both adapted to contain water, said pressure chamber connected to said heating chamber, at least one pressure adjusting means, gases supplying means supplying pressurised gases to said at least one pressure regulating means, said at least one pressure adjusting means being located between said heating chamber and said gases supplying means, and adapted to convert said pressurised gases from said gases supply means to at least a first gas of a first pressure and a second gas of a second pressure where said first gas is supplied to said heating chamber and said second gas is supplied to said pressure chamber, such that said first and said second gas have a pressure difference substantially large enough to cause water to flow from said pressure chamber to said heating chamber.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the forgoing and also envisages constructions of which the following gives examples.

BRIEF DESCRIPTION OF THE DRAWINGS

One preferred form of the present invention will now be described with reference to the accompanying drawings.

DETAILED DESCRIPTION OF THE PREFERRED EMBODIMENTS

The preferred embodiment of the present invention generally consists of four pieces of apparatus to provide a breathing assistance apparatus which has a pressure controlled water auto feed to a humidifier chamber. Firstly, a gases supply means, for example a compressor or blower, provides gases to a humidifier, the gases exiting the gases supply means having a varied pressure. Secondly, a pressure adjusting means consisting of pressure regulators, conduits with specific diameters or both, that regulate the gases from the blower to at least one different pressure. Thirdly, a heating chamber receives gases from the pressure adjusting means. Fourthly, a water reservoir or a pressure chamber receives gases of higher pressure (compared to the pressure of the gases received by the heating chamber) from the pressure adjusting means. In addition, a series of pipes or conduits are supplied to connect the pieces of apparatus together to form an operational system.

Figure 1:
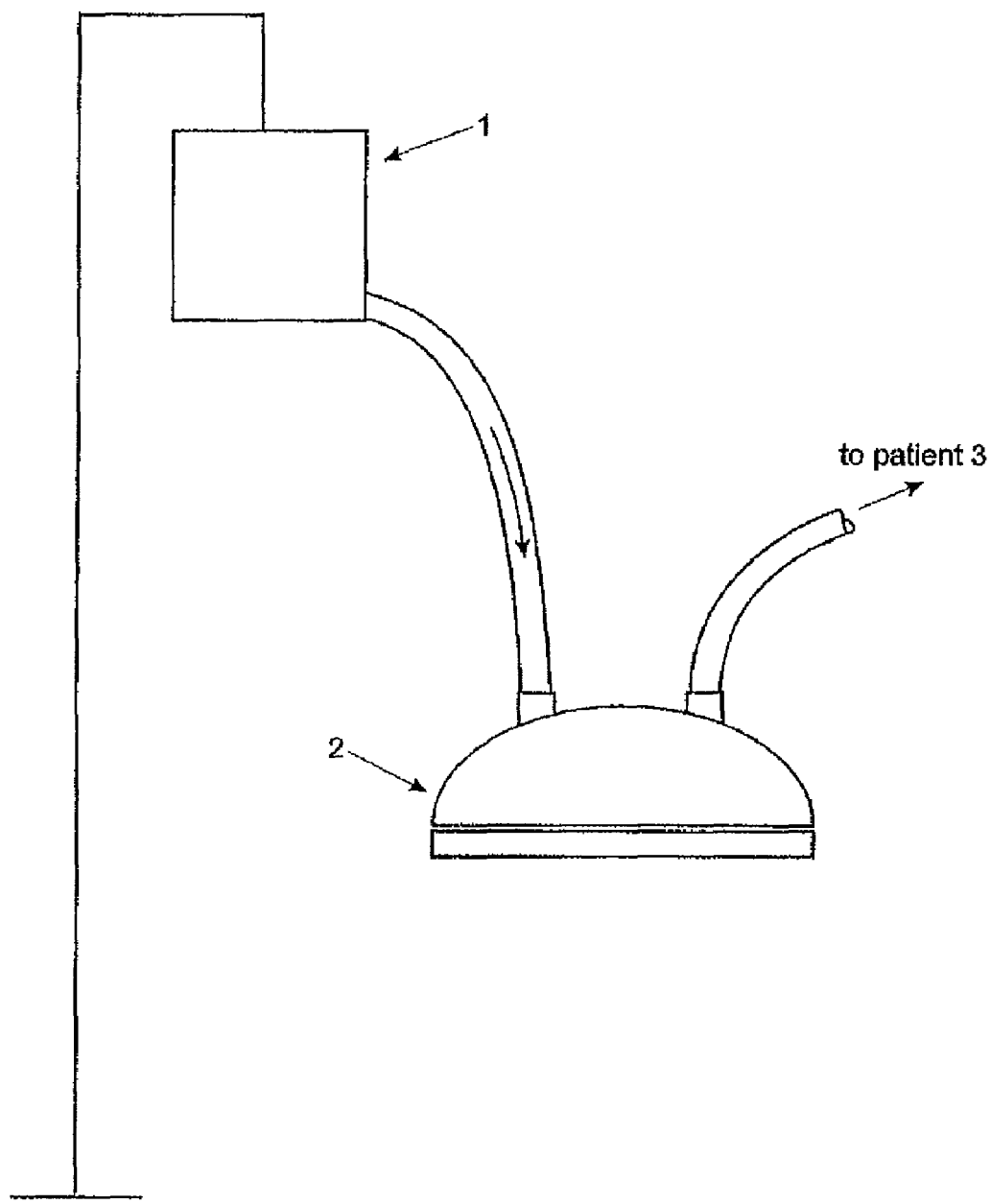
FIG. 1 is an illustration of a typical prior art humidifier including a gravity feed humidifying chamber.
Figure 2:
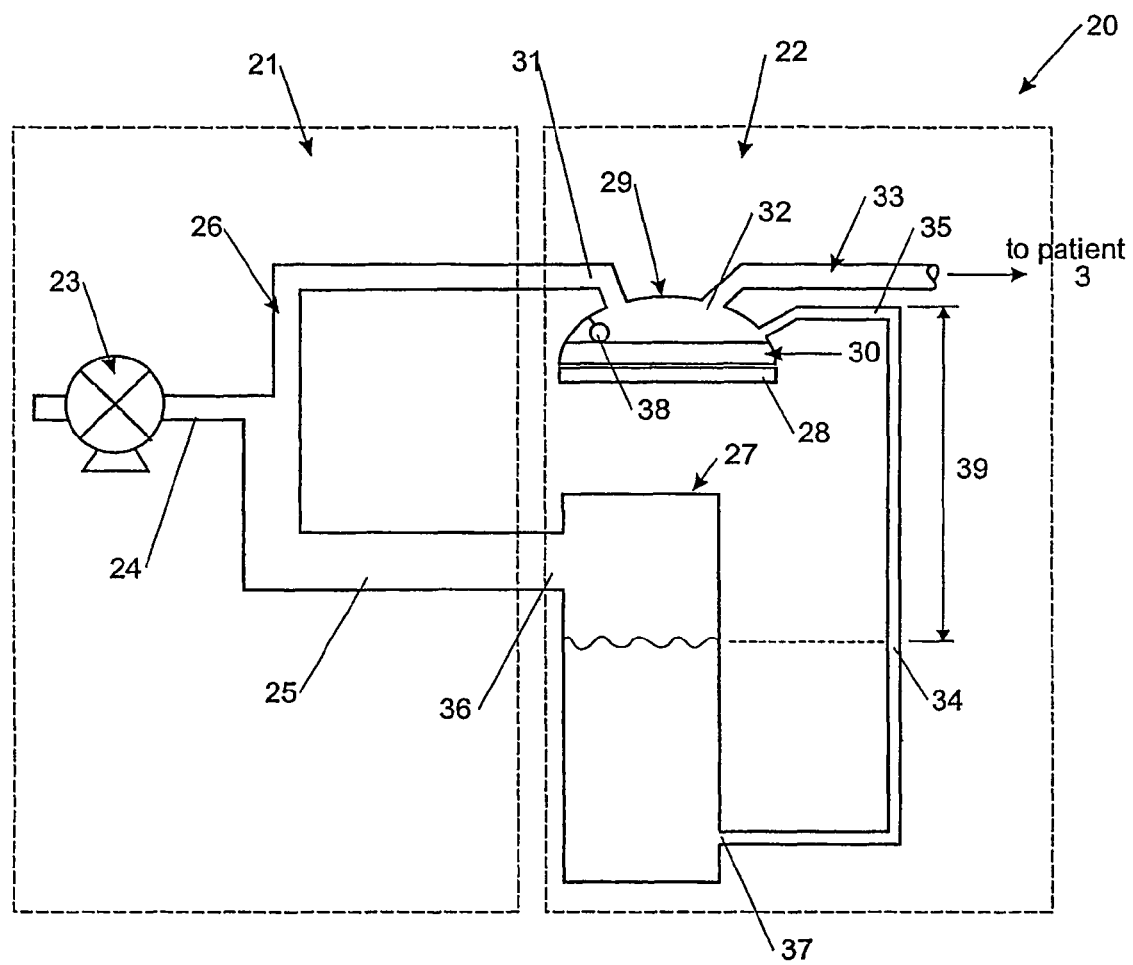
FIG. 2 is an illustration of the preferred embodiment of the breathing assistance apparatus of the present invention.

FIG. 2 shows the breathing assistance apparatus 20 of the present invention as it might be used in a hospital. The breathing assistance apparatus 20 comprises a pressure regulating section 21 and a pressure differential section 22. The output of the apparatus 20 is supplied to a patient 3.

In the preferred embodiment of the breathing assistance apparatus 20, the pressure regulating section 21 consists of a blower 23 and a series of conduits 24, 25, 26. The pressure differential section 22 consists of a humidifier including heating or humidification chamber 29, a pressure chamber 27, a transfer pipe 34 and an output conduit 33 supplying the patient 3.

The heating chamber 29 consists of three ports, a pressurised gases input port 31, a water supply inlet 35 and a heated humidified pressurised output port 32. The heating chamber 29 is adapted to contain water, and a float 38 controls the level of the water within the chamber 29. A heater plate 28 heats the water within the chamber 29. The operation of a humidification chamber 29 and float 33 is known and is described in Fisher and Paykel Limited U.S. Pat. No. 4,913, 140, the contents of which are included herein.

The pressure chamber 27 is a water reservoir having a gases inlet port 36 and water outlet port 37. The pressure chamber 27 is adapted to be refillable either manually through the gases inlet 36 or by other appropriate means.

The blower 23 is a standard type of blower typically used for breathing circuits that produces pressurised gases. The pressurised gases exit the blower, travels along the conduit 24 until it reaches a T junction where it diverts into two separate routes along two conduits 25, 26. Therefore, pressurised gases exiting from the blower 23 are split and diverted through each of the two conduits 25, 26, which pass pressurised gases to the pressure differential section 22. In particular, the first inlet conduit 25 passes pressurised gases to the pressure chamber 27 and the second inlet conduit 26 passes pressurised gases to the humidification chamber 29. The humidification chamber 29 is in use at least partially filled with water 30 and the chamber 29 is heated by the heater plate 28, similar to prior art humidification chambers. As the pressurised gases from the second inlet conduit 26 enter the chamber 29 via the chamber entry port 31 and pass through the chamber 29, the gases are heated and humidified. The heated and humidified gases then exit through the exit port 32 and are passed through an outlet conduit 33 to the patient 3.

A correct level of water within the reservoir feeding the humidification chamber 29 must be maintained to ensure the patient 3 is continuously receiving heated and humidified gases. For water to flow from the pressure chamber water reservoir 27 to the humidification chamber 29, in order to maintain the correct level of water within the humidification chamber 29, the pressure within the pressure chamber water reservoir 27 must be greater than the pressure within the humidification chamber 29 plus the head of water. To ensure an adequate flow, the pressure in the pressure chamber water reservoir 27 must be greater than the pressure in the humidification chamber 29. One way to ensure this occurs is for the diameter of the second inlet conduit 26 to the humidifier chamber 29 to be smaller than the diameter of the first inlet conduit 25 to the pressure chamber water reservoir 27.

In use, when the blower 23 is switched on pressurised gases pass through conduits 24, 25, 26 and into the pressure chamber 27 and humidification chamber 29, thereby each of the chambers 27, 29 are pressurised. As the second inlet conduit 26 is smaller in diameter than the first inlet conduit 25, the pressure in the pressure chamber 27 is higher then the pressure in the humidification chamber 29 causing water to be forcibly pushed to the bottom of the pressure chamber 27, out the exit port 37 and into the transfer pipe 34. As the transfer pipe 34 is connected between the pressure chamber 27 and the heating chamber 29 water flows through the transfer pipe 34 and into the humidification chamber 29. Preferably the transfer pipe 34 allows only a one way flow from the pressure chamber 27 to the heating chamber 29.

The pressure difference between the humidification chamber 29 and pressure chamber 27 is such that the water may travel against gravity by a predetermined height 39. The height 39 that the water can travel is called the "head"; this is the height difference 39 between the water level in the pressure chamber 27 and the top of the transfer pipe 34 (the maximum height that the water will reach). When the water reaches the exit of the transfer pipe 34, it enters the humidification chamber 29, thereby maintaining a steady flow of water into the humidification chamber 29.

As discussed earlier, the level of the water in the humidification chamber 29 is controlled by a float 38. Once the level of the water reaches a predetermined level, the float 38 causes a valve, positioned on the entrance of the water feed pipe 35, to shut off the water feed pipe, preventing any water entering the humidification chamber 29. In most cases, the float 38 is lifted by the water and shuts off the valve itself.

Figure 3:
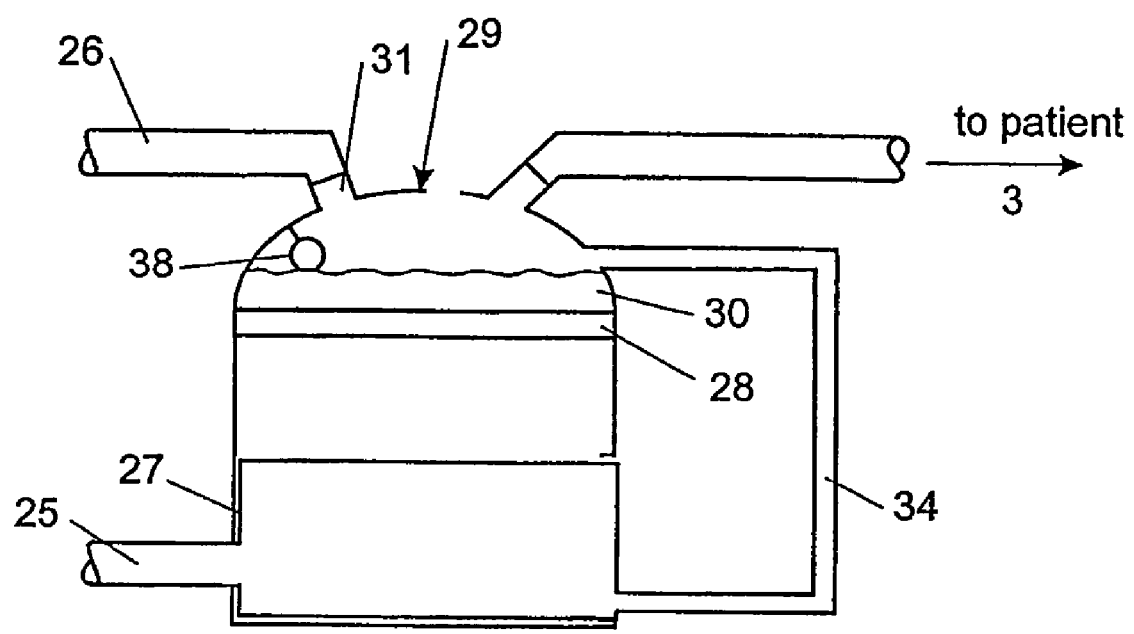
FIG. 3 is an illustration of the preferred form of breathing assistance apparatus of the present invention where the pressure chamber is a removable tray.

Referring to FIG. 3, in the preferred form the present invention, the pressure chamber water reservoir 27 is a removable tray located below the heater plate 30 and humidification chamber 29. This tray is removable so to improve the access to the water reservoir for quick and efficient refilling. The coupling between the water reservoir tray 39 and the humidification chamber 29 is a coupling or joint that can be made so that when the humidification chamber 29 and pressure chamber 27 are under pressure water is prevented from leaking from the water reservoir tray 39 and couplings or joints.

Figure 4:
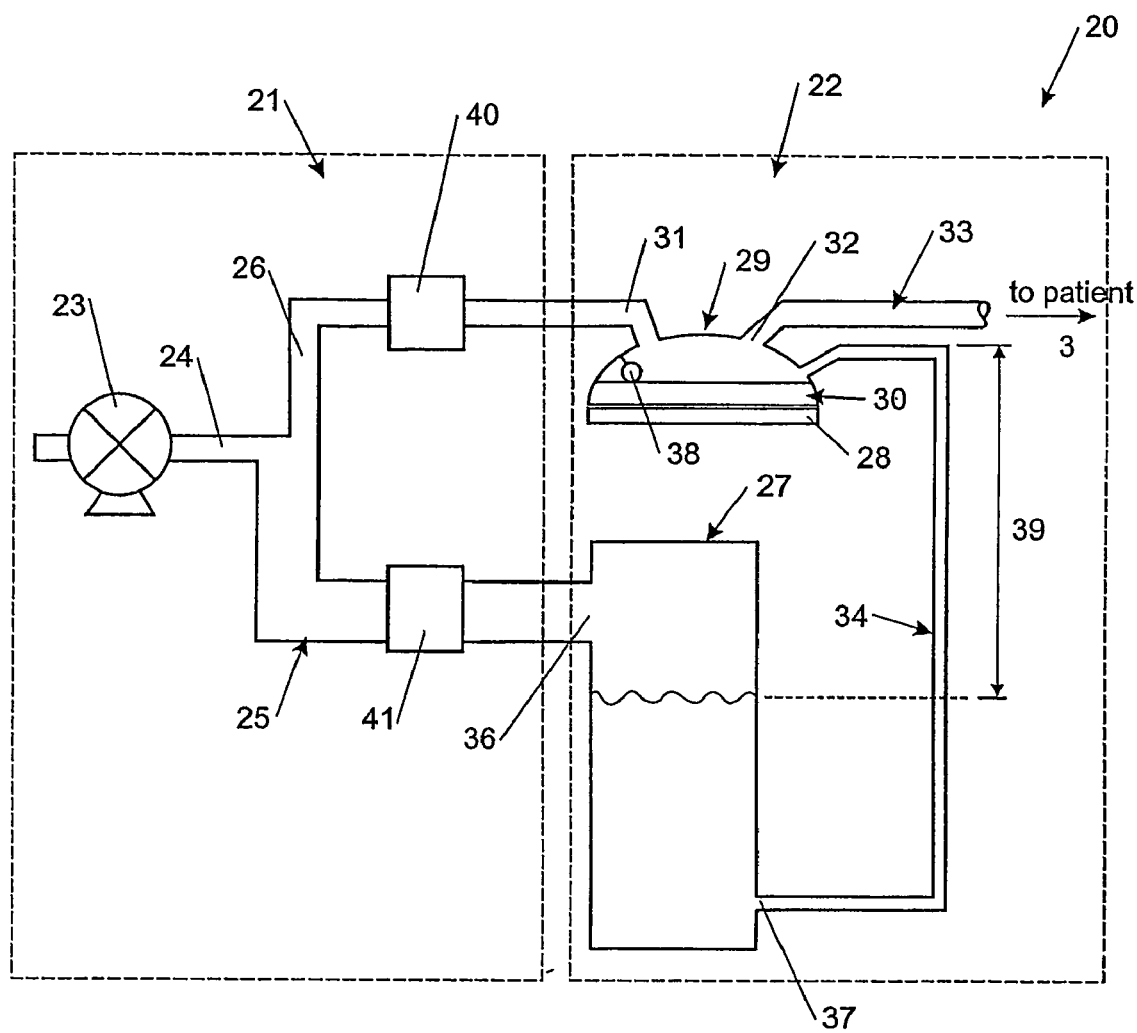
FIG. 4 is an illustration of the breathing assistance apparatus of the present invention including pressure regulators.

Referring to FIG. 4 where an alternative embodiment of the present invention is shown. The blower 23 provides a primary pressure to conduits 24, 25, 26. This primary pressure is likely to fluctuate with the gases flow fluctuations. Therefore the pressures in the chambers 27, 29 are likely to vary, and so the pressure differential between the chambers 27, 29 will vary also. To ensure a steady or constant pressure differential between the humidification chamber 29 and pressure chamber 27, a regulator may be each placed in the path of the first inlet conduit 25 and second inlet conduit 26. These regulators 40, 41 regulate the pressure in the conduits 25, 26 ensuring a constant pressure differential. They may also prevent any pressurised air from flowing back towards the blower 23 and travelling back down either of the conduits 25, 26.

The advantages provided by the breathing assistance apparatus of the present invention are as follows. Water is supplied to the humidification chamber 29 in a controlled manner and a water level that allows for appropriate humidification of the gases passing through the humidifier and passing to the patient is maintained. In some forms of the present invention a large water reservoir may be maintained in the pressure chamber 27, therefore the reservoir only needs to be filled up less regularly than what is currently used and known in the prior art. The location of the heating chamber 29 and pressure chamber 27 is also more flexible than prior art devices. In particular, the pressure chamber 27 including the water reservoir can be located level with or below the humidification chamber 29. This means that the pressure chamber 27 may be placed out of the way, for example under a hospital bed, as opposed to in an overhead position. Furthermore, the pressure chamber 27 can be placed at a distance away from the humidification chamber 29 as long as there is sufficient pressure differential between the chambers 27, 29 so that water will flow from the pressure chamber 27 to the humidification chamber 29.

We claim:

1. An apparatus for supplying gases at a pressure above atmospheric to a patient for therapeutic purposes, comprising:

a heating chamber adapted to contain water and having an inlet adapted to receive gases, and inlet for receiving water, an outlet, and a heater plate on a lower surface thereof;

a pressure chamber adapted to contain water and having an inlet adapted to receive gases and an outlet;

a pressurised gases supply adapted to supply said pressurised gases to said pressure chamber inlet via a first conduit and to said heating chamber inlet via a second conduit, a water transfer pipe connected between said pressure chamber outlet and said heating chamber and adapted to allow water to flow through said water transfer pipe and into said heating chamber;

a pressure regulator located in said second conduit operable to convert gas from said pressurised gas supply at a first pressure above atmospheric to a second pressure above atmospheric, said first pressure greater than said second pressure, said gases at said second pressure flowing from said heating chamber inlet, across the surface of said water to said heating chamber outlet;

an output conduit adapted to connect to said heating chamber outlet for supplying said second gas to the patient;

said first gas and said second pressure having a pressure differential large enough to cause water to flow from said pressure chamber to said heating chamber; and a valve on said water transfer pipe, said valve adapted to maintain a substantially consistent water level in said heating chamber.

2. An apparatus according to claim 1 wherein said pressure regulator comprises a first conduit to convert gas from said pressurised gas supply to said first gas and a second conduit to convert gas to said second gas.

3. An apparatus according to claim 2 wherein said second conduit has a substantially larger diameter than said first conduit.

4. An apparatus according to claim 1 wherein said pressure regulator includes a second pressure regulator and a third pressure regulator to adjust and maintain the gases pressure flowing to said heating chamber and said pressure chamber.

5. An apparatus according to claim 1 wherein said pressure chamber is a water reservoir.

6. An apparatus according to claim 5 wherein said water reservoir is a removable tray located below said heater plate.

* * * * *